United States Patent [19]

Hall et al.

[11] 3,987,803

[45] Oct. 26, 1976

[54] NOVEL PROCESS FOR ALTERING THE ORGANOLEPTIC PROPERTIES OF TOBACCO USING 2-METHYL-4-PENTENOIC ACID AND THE ETHYL ESTERS THEREOF

[75] Inventors: John B. Hall, Rumson; Ching Y. Tseng, Middletown; Manfred Hugo Vock, Locust; Joaquin Vinals, Red Bank, all of N.J.; Edward J. Shuster, Brooklyn, N.Y.

[73] Assignee: International Flavors & Fragrances Inc., New York, N.Y.

[22] Filed: Apr. 21, 1975

[21] Appl. No.: 569,854

Related U.S. Application Data

[63] Continuation-in-part of Ser. No. 490,718, July 22, 1974, Pat. No. 3,907,718.

[52] U.S. Cl. ............................. 131/17 R; 131/144
[51] Int. Cl.² ........................................ A24B 3/12
[58] Field of Search ............ 131/2, 144, 17; 99/140

[56] References Cited

UNITED STATES PATENTS

| | | | |
|---|---|---|---|
| 3,499,769 | 3/1970 | Kratz et al. | 99/140 |
| 3,764,349 | 10/1973 | Mookherjee et al. | 131/144 UX |

OTHER PUBLICATIONS

"Dangerous Prop. of Ind. Mat." by Sax; 3rd Edit; 1968 p. 1069 cited.

*Primary Examiner*—Robert W. Michell
*Assistant Examiner*—V. Millin
*Attorney, Agent, or Firm*—Arthur L. Liberman; Harold Haidt

[57] ABSTRACT

Described is a process comprising adding to tobacco (for subsequent incorporation into smoking articles along with tobacco blend) an amount sufficient to alter the flavor or aroma of the tobacco of 2-methyl-4-pentenoic acid and/or ethyl-2-methyl-4-pentenoate.

2 Claims, No Drawings

NOVEL PROCESS FOR ALTERING THE ORGANOLEPTIC PROPERTIES OF TOBACCO USING 2-METHYL-4-PENTENOIC ACID AND THE ETHYL ESTERS THEREOF

This application is a continuation-in-part of U.S. application for Letters Patent, Ser. No. 490,718, filed on July 22, 1974 now U.S. Pat. No. 3,907,718 issued on Sept. 23, 1975.

BACKGROUND OF THE INVENTION

This invention relates to novel tobacco products, novel tobacco flavoring compositions, and processes for producing same, and has for an object the provision of a composition and process for improving the flavor and aroma of tobacco and tobacco smoke.

It is well known in the tobacco art that the flavor and aroma of the tobacco product and the smoke from the tobacco are very important considerations insofar as the ultimate consumer is concerned. Considerable efforts have been and are being exerted by the manufacturers of tobacco products to provide a product that will be both acceptable to the consumer, particularly as regards flavor and aroma characteristics, on smoking. Notes having Turkish-like characteristics as well as aromatic, sweet, sour, bitter, fruity, green and strawberry notes are desirable in tobacco flavoring compositions.

U.S. Pat. No. 3,499,769 issued on Mar. 10, 1970, discloses processes for imparting a fruity flavor (particularly strawberry flavor) to foods by adding a small amount of 2-methyl-4- pentenoic acid to the foodstuff. In U.S. Pat. No. 3,499,769 it is emphasized that the basic nuance imparted by the 2-methyl-2-pentenoic acid is a "berry" flavor.

Quite unexpectedly, the 2-methyl-4-pentenoic acid and esters thereof of the instant invention have properties different in kind from the 2-methyl-2-pentenoic acid of U.S. Pat. No. 3,499,769 which is only fruity and strawberry-like and does not have the tobacco flavor enhancing qualities of the 2-methyl-4-pentenoic acid and esters thereof of the instant invention.

Arctander, "Perfume and Flavor Chemicals", 1969 discloses the use in perfume compositions and flavors of 4-pentenoic acid, thus:

". . . only rarely used in perfume compositions mainly on fruity bases and certain artificial essential oils.

It finds use in flavors on account of its sour-caramellic taste, pleasant at levels below 10 ppm, and including an almost sweet aftertaste. Higher concentrations have acrid taste and repulsively acid odor, pungent and irritating.

Traces, equivalent to 1 to 5 ppm, are used in imitation butter flavor and in various fruit flavor complexes, e.g., apple, pineapple, apricot and strawberry."

at Volume II, No. 2452. Arctander also discloses the use of trans-2 -methyl-2-butenoic acid (tiglic acid) at Vol. II, No. 2949 in perfumery:

"Spicy-rooty, sweet-sour herbaceous odor of moderate tenacity."

and the use of cis-2-methyl-2-butenoic acid (angelic acid) and alkyl esters thereof in perfumes and flavors at Vol. I, No. 238.

The alkenoic acids and esters thereof of the prior art are considered to be different in kind from the 2-methyl-4-pentenoic acid and $C_2$–$C_6$ alkyl esters thereof of the instant invention insofar as their organoleptic properties are concerned.

THE INVENTION

It has now been discovered that novel tobacco compositions having Turkish-like characteristics as well as aromatic, sweet, sour, bitter, fruity, green and strawberry notes, may be provided by the utilization of 2-methyl-4-pentenoic acid and/or ethyl-2-methyl-4-pentenoate having the generic formula:

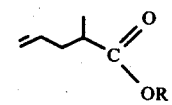

wherein R is hydrogen, or ethyl.

The 2-methyl-4-pentenoic acid and ethyl-2-methyl-4-pentenoate, so useful, may be produced according to the process comprising the steps of first reacting 1,1,1-triethoxy-propane with 2-propenol-1 to form ethyl-2-methyl-4-pentenoate; then, in the alternative, (i) using the thusformed ethyl-2-methyl-4-pentenoate as such for its own organoleptic characteristics as a tobacco flavor adjuvant or enhancer, or (ii) saponifying the ethyl-2-methyl-4-pentenoate with base to form a salt of 2-methyl-4-pentenoic acid and then acidifying the salt of 2-methyl-4-pentenoic acid with acid to form 2-methyl-4-pentenoic acid itself and using the said 2-methyl-4-pentenoic acid for its own organoleptic characteristics as a tobacco flavor adjuvant or enhancer.

The 2-methyl-4-pentenoic acid and ethyl-2-methyl-4-pentenoate may also be produced according to the process comprising the steps of first reacting 1,1,1-triethoxy propane with 2-propynol-1 to form ethyl-2-methyl-3,4-pentadienoate; then, in the alternative, either (i) hydrogenating with hydrogen gas the thus-formed ethyl-2-methyl-3,4-pentadienoate in the presence of a palladium-on-carbon catalyst or a palladium-on-calcium carbonate catalyst, thereby forming a reaction mixture containing ethyl-2-methyl-4-pentenoate and using this material as such for its own organoleptic characteristics as a tobacco flavor adjuvant or enhancer, or (ii) recovering the ethyl-2-methyl-4-pentenoate and using the thus-recovered material for its own organoleptic characteristics or (iii) saponifying the ethyl-2-methyl-4-pentenoate with base to form a salt of 2-methyl-4-pentenoic acid and then acidifying the salt of 2-methyl-4-pentenoic acid with acid to form the 2-methyl-4-pentenoic acid itself and using the said 2-methyl-4-pentenoic acid for its organoleptic characteristics as a tobacco flavor adjuvant or enhancer.

The 2-methyl-4-pentenoic acid and and ethyl ester of 2-methyl-4-pentenoic acid of our invention having the generic formula:

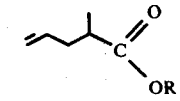

wherein R is hydrogen or ethyl, is intended to include singly, and in admixture the two stereoisomers of 2-methyl-4-pentenoic acid and its ethyl ester, having the structures:

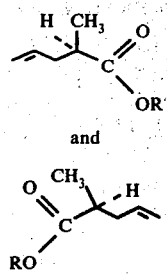

wherein R is hydrogen or ethyl.

One process for producing the chemical compounds useful in practicing our invention involves the steps of:

a. First reacting 1,1,1-triethoxypropane with 2-propanol-1 in the presence of a phosphoric acid catalyst to form ethyl-2-methyl-4-pentenoate. The reaction temperature range is 100°–225° C with a range of 140°–180° C being preferred. The mole ratio of reactants preferred is 1:1, with a large excess of 2-propanol-1 undesirable and a large excess of triethoxypropane being uneconomical. The reaction time is inversely dependent upon the temperature of reaction. Thus, for example, where the temperature range of reaction is 165°–185° C, the reaction time is approximately three (3) hours. As stated, supra, the reaction product, ethyl-2-methyl-4-pentenoate may be used as is, or it may further be reacted as in step (b) set forth infra; but in any event, the reaction product is "worked-up" by first neutralizing the acid catalyst, the phosphoric acid, using base (e.g., sodium bicarbonate) and then fractionally distilling the reaction product.

b. If desired, the resulting ethyl-2-methyl-4-pentenoate may be converted into 2-methyl-4-pentenoic acid by the standard saponification and acidification reactions. The saponification is preferably carried out using strong aqueous base, e.g., 50% aqueous sodium hydroxide or 50% aqueous potassium hydroxide admixed with methanol. After acidification of the resulting salt of 2-methyl-4-pentenoic acid (e.g., the sodium or potassium salt) using mineral acid (e.g., 6 molar aqueous hydrochloric acid) the 2-methyl-4-pentenoic acid is extracted from the aqueous phase using an organic solvent such as toluene. The organic solvent is then stripped from the acid and the acid is fractionally distilled.

The foregoing series of reactions may be illustrated as follows:

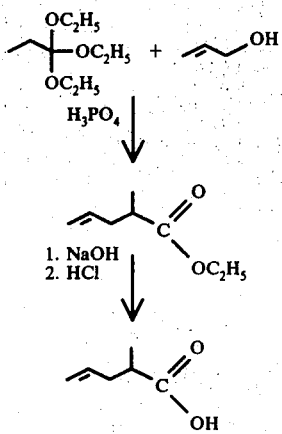

A second process for producing the chemical compounds useful in practicing our invention involves the steps of:

a. First reacting 1,1,1-triethoxy propane with 2-propane-1 in the presence of a propionic acid catalyst thereby forming ethyl-2-methyl-3,4-pentadienoate. The reaction temperature range is 120°–180° C with a range of 145–150° C being preferred. The mole ratios of reactants preferred is 1:1 with a slight excess of either reactant permissible. A large excess of 2-propynol-1 is undesirable, and a large excess of the triethoxy propane is uneconomical. The percentage of propionic acid catalyst may vary from 1 up to 3%, but a 2% concentration of catalyst is preferred. Since the reaction temperature is in the range of 120°–180° C higher pressures of reaction are required for the carrying out of the reaction, and, accordingly, pressures of from 30 up to 100 psig are used. The reaction time is inversely dependent on the temperature of reaction. Thus, for example, where the temperature range of reaction is 150°–160° C, the reaction time is approximately 3 hours. The reaction time period varies between 2 and 6 hours, and a reaction time of 3–4 hours is preferred. The reaction product, the ethyl-2-methyl-3,4-pentadienoate, is then "worked-up" and this "work-up" operation is performed by first, if necessary, washing out the excess triethyl orthopropionate reactant by washing with a dilute (e.g., 5%) hydrochloric acid solution. The acid is then neutralized by use of a sodium bicarbonate wash, and the reaction mass is then fractionally distilled.

b. The resulting ethyl-2-methyl-3,4-pentadienoate is then reacted with hydrogen in the presence of a palladium-on-carbon catalyst or a "Lindlar" catalyst (palladium-on-calcium carbonate). The percentage of palladium on carbon or on calcium carbonate varies from about 2% up to about 7% with a percentage of palladium-on-carbon or on calcium carbonate being preferred to be about 5%. The temperature of reaction for this hydrogenation may vary from about 10° C up to about 50° C with a preferred reaction temperature of 25°–35° C. Since the reaction is exothermic, it is usually necessary to provide external cooling to the reaction mass during the course of the reaction. The pressure of hydrogen over the reaction mass may vary from about 5 psig up to about 50 psig, with the most preferred pressure being 20 psig. It has been found that pressures above 20 psig give rise to larger amounts of undesired side products. The hydrogenation reaction may be carried out in the presence of or in the absence of a solvent. When a solvent is used, it is required that it be an inert (non-reactive) solvent such as ethanol. If a solvent is used, it is preferred that the mole ratio of solvent:pentadienoate ester be approximately 1:1. The percentage of catalyst in the reaction mass may vary from 0.125% up to about 2.0% with a percentage of catalyst of about 0.25% being preferred. When using a Lindlar catalyst, the hydrogenation reaction produces a mixture of ethyl-2-methyl-cis-3-pentenoate and ethyl-2-methyl-4-pentenoate in the ratio of from about 6:4 up to about 7:3. As a result, the desired ethyl-2-methyl-4-pentenoate for use in the instant invention may, if desired, be enriched with respect to the ethyl-2-methyl-4-pentenoate by means of fractional distillation or the mixture resulting may be used as such for its organoleptic properties as a tobacco flavor adjuvant or enhancer. Where the catalyst used is palladium-on-carbon rather than a Lindlar catalyst (palladium-on-calcium carbonate), a mixture of ethyl-2-methyl-cis-3-pentenoate, ethyl-2-methyl-4-pentenoate and ethyl-2-methyl-pentanoate is formed which may be used as such for its organoleptic properties as a tobacco flavor adjuvant or enhancer or which may be separated as by means of fractional distillation. In any event, at the end of the hydrogenation reaction, the reaction mass is filtered in order to separate catalyst from liquid phase desired product, and the filtrate is distilled using a fractional distillation column operated under vacuum.

c. If desired, the resulting ethyl-2-methyl-4-pentenoate and other esters which have not been separated therefrom after the hydrogenation reaction may be converted into 2-methyl-4-pentenoic acid and other acids by means of standard saponification and acidification reactions. The saponification is preferably carried out using strong aqueous base, e.g., 50% aqueous sodium hydroxide or 50% aqueous potassium hydroxide admixed with methanol. After acidification of the resulting salt of 2-methyl-4-pentenoic acid (e.g., the sodium or potassium salt) using mineral acid, the 2-methyl-4-pentenoic acid is extracted from the aqueous phase using an organic solvent such as diethyl ether. The organic solvent is then stripped from the acid, and the acid is fractionally distilled.

The foregoing series of reactions may be illustrated as follows:

(a)

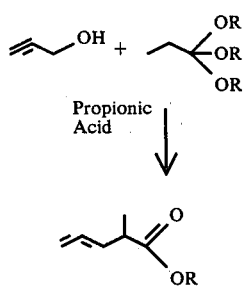

Propionic Acid (b)

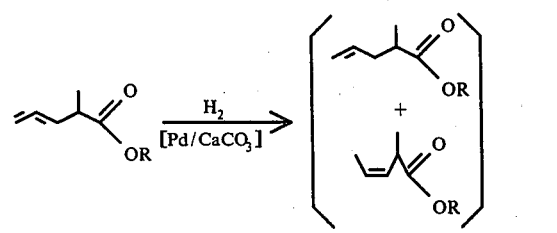

or

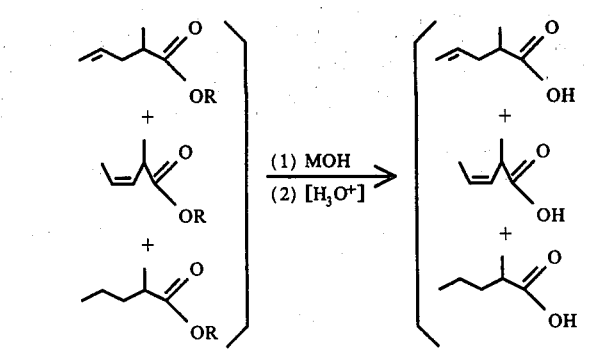

(c)

wherein R is ethyl and M is alkali metal.

Examples of specific reaction products, the uses of which are contemplated within the scope of our invention, and their respective organoleptic properties are set forth in the following table:

| Compound | Flavor Properties |
| --- | --- |
| Ethyl-2-methyl-4-pentenoate | Sweet, fruity, strawberry-like and slightly green aroma. At 100 ppm and 200 ppm, on smoking, more aromatic, less harsh, Turkish tobacco-like. |
| 2-methyl-4-pentenoic acid | Pungent, sweet, fruity, sour and green notes. At 100 ppm and 200 ppm, on smoking, sweeter and Oriental, Turkish-like aroma. |

Our invention provides an organoleptically improved smoking tobacco product and additives therefor, as well as methods of making the same which overcome specific problems heretofore encountered in which specific desired Turkish and/or Oriental flavor characteristics of tobacco are created or enhanced and may be readily controlled and maintained at the desired uniform level regardless of variations in the tobacco components of the blend.

This invention further provides improved tobacco additives and method whereby various desirable Turkish and/or Oriental flavoring characteristics may be imparted to smoking tobacco products and may be readily varied and controlled to produce the desired uniform flavoring characteristics.

In carrying out our invention we add to smoking tobacco materials or a suitable substitute therefor (e.g., dried lettuce leaves) an aroma and flavor additive containing as an active ingredient one or both of the following materials:

i. 2-Methyl-4-pentenoic acid;
 ii. Ethyl-2-methyl-4-pentenoate

In addition to the 2-methyl-4-pentenoic acid and/or ethyl-2-methyl-4-pentenoate of our invention other flavoring and aroma additives may be added to the smoking tobacco material or substitute therefor either separately or in mixture with the 2-methyl-4-pentenoic acid and/or ethyl-2-methyl-4-pentenoate as follows:

I. Synthetic Materials
Beta-Ethyl-Cinnamaldehyde
Eugenol
Dipentene
Maltol
Ethyl Maltol
Delta Undecalactone
Delta Decalactone
Benzaldehyde
Amyl Acetate
Ethyl Butyrate
Ethyl Valerate
Ethyl Acetate
2-Hexehol-1,2-methyl-5-isopropyl-1,3-nonadiene-8-one
2,6-Dimethyl-2,6-undecadiene-10-one
2-Methyl-5-isopropyl acetophenone
2-Hydroxy-2,5,5,8a-tetramethyl-1-(2-hydroxyethyl)-decahydronaphthalene
Dodecahydro-3a-6,6,9a-tetramethyl naphtho-(2,1-b)-furan
4-Hydroxy hexanoic acid, gamma lactone
Polyisoprenoid hydrocarbons defined in Example V of U.S. Pat. No. 3,589,372 issued on June 29, 1971
II. Natural Oils
Celery seed oil
Coffee extract
Bergamot oil
Cocoa extract
Nutmeg oil
Origanum oil An aroma and flavoring concentrate containing 2-methyl-4-pentenoic acid and/or ethyl-2-methyl-4-pentenoate and, if desired, one or more of the above indicated additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste but insofar as enhancement or the imparting of natural and/or sweet notes, we have found that satisfactory results are obtained if the proportion by weight of the sum total of 2-methyl-4-pentenoic acid and/or ethyl-2-methyl-4-pentenoate to smoking tobacco material is between 50 ppm and 250 ppm (0.005%–0.025%) of the active ingredients to the smoking tobacco material. We have further found that satisfactory results are obtained if the proportion by weight of the sum total of 2-methyl-4-pentenoic acid and/or ethyl-2-methyl-4-pentenoate used to flavoring material is between 0.02% and 5%.

Any convenient method for incorporating the 2-methyl-4-pentenoic acid and/or ethyl-2-methyl-4-pentenoate in the tobacco product may be employed. Thus, the 2-methyl-4-pentenoic acid and/or ethyl-2-methyl-4-pentenoate taken alone or along with other flavoring additives may be dissolved in a suitable solvent such as ethanol, pentane, diethyl ether and/or other volatile organic solvents and the resulting solution may either be spread on the cured, cased and blended tobacco material or the tobacco material may be dipped into such solution. Under certain circumstances, a solution of the 2-methyl-4-pentenoic acid and/or ethyl-2-methyl-4-pentenoate taken alone or taken further together with other flavoring additives as set forth above, may be applied by means of a suitable applicator such as a brush or roller on the paper or leaf wrapper for the smoking product, or it may be applied to the filter by either spraying, or dipping or coating.

Furthermore, it will be apparent that only a portion of the tobacco or substitute therefor need be treated and the thus treated tobacco may be blended with other tobacco before the ultimate tobacco product is formed. In such cases, the tobacco treated may have the 2-methyl-4-pentenoic acid and/or ethyl-2-methyl-4-pentenoate in excess of the amounts or concentrations above indicated so that when blended with other tobaccos, the final product will have the percentage within the indicated range.

In accordance with one specific example of our invention an aged, cured and shredded domestic burley tobacco is spread with a 20% ethyl alcohol solution of a mixture of 50% 2-methyl-4-pentenoic acid and 50% ethyl-2-methyl-4-pentenoate in an amount to provide a tobacco composition containing 100 ppm by weight of 2-methyl-4-pentenoic acid and 100 ppm by weight of ethyl-2-methyl-4-pentenoate on a dry basis. Thereafter, the alcohol is removed by evaporation and the tobacco is manufactured into cigarettes by the usual techniques. The cigarette when treated as indicated has a desired and pleasing aroma which is detectable in the main and side streams when the cigarette is smoked. This aroma is described as a "Turkish/Oriental" tobacco aroma.

While our invention in particularly useful in the manufacture of smoking tobacco, such as cigarette tobacco, cigar tobacco and pipe tobacco, other tobacco products formed from sheeted tobacco dust or fines may also be used. Likewise, the 2-methyl-4-pentenoic acid and/or ethyl-2-methyl-4-pentenoate of our invention can be incorporated with materials such as filter tip materials, seam paste, packaging materials and the like which are used along with tobacco to form a product adapted for smoking. Furthermore, the 2-methyl-4-pentenoic acid and/or ethyl-2-methyl-4-pentenoate can be added to certain tobacco substitutes of natural or synthetic origin (e.g., dried lettuce leaves) and, accordingly, by the term "tobacco" as used throughout this specification is meant any composition intended for human consumption by smoking or otherwise, whether composed of tobacco plants parts or substitute materials or both.

The following examples are given to illustrate embodiments of the invention as it is presently preferred to practice it. It will be understood that these examples are illustrative, and the invention is not to be considered as restricted thereto except as indicated in the appended claims. All parts and percentages given herein are by weight unless otherwise specified.

EXAMPLE I

Preparation of Ethyl-2-Methyl-4-Pentenoate

To a two liter autoclave, the following materials are added:

| | |
|---|---|
| Triethyl orthopropionate (1,1,1-triethoxypropane) | 495 g (2.4 moles) |
| Allyl alcohol | 140 g (2.4 moles) |
| Phosphoric acid (85 %) | 12 g |

The autoclave is sealed and the mixture is heated with stirring at 165°–185° C for a period of three hours.

The autoclave is then opened and 12.6 g sodium bicarbonate is added to the reaction mass in order to neutralize the phosphoric acid. 30 g Primol (a registered trademark for mineral oil manufactured by the Exxon Co. of Linden, N.J.) is then added as a still base, and the reaction mass is fractionally distilled on a 1 inch × 20 inch packed Goodloe distillation column (i) at atmospheric pressure and 129° C (yielding a mixture of ethanol and ethyl propionate (245 g) and (ii) at 40 mm Hg. pressure and 75° C (yielding 264 g of ethyl-2-methyl-4-pentenoate. Yield, based on triethyl orthopropionate used, 73.5%.

Mass spectral analysis: m/e = 69, 41, 29, 27 39 and 68.

| NMR Analysis | Interpretation | |
|---|---|---|
| 1.16 ppm (d) | $CH_3-\overset{H}{\underset{\underset{O}{\parallel}}{C}}-C-$ | 6H |
| 1.20 (t) | $CH_3-CH_2-O-\underset{\underset{O}{\parallel}}{C}-$ | |
| 2.64–2.08 (m) | $=C-CH_2 + H\underset{\underset{O}{\parallel}}{C}-$ | 3H |
| 4.12 (q) | $Me-CH_2-O-\underset{\underset{O}{\parallel}}{C}-$ | 2H |
| 5.18–4.98 (m) | $HC=CH_2$ | 2H |
| 5.98–5.56 (m) | $HC=CH_2$ | 1H |

IR Analysis
915 cm$^{-1}$
1015
1090
1140
1175
1225
1240
1380
1460
1730
2940
2980

EXAMPLE II

Preparation of 2-Methyl-4-Pentenoic Acid

Into a 250 ml flask equipped with magnetic stirrer, the following materials are added:

| | |
|---|---|
| Ethyl-2-methyl-4-pentenoate (prepared according to Example I) | 80 g |
| 50 % Aqueous NaOH | 70 g |
| Methanol | 100 ml |

Over a four-hour period, the mixture is stirred at 30°–50° C. At the end of the four-hour period, 200 ml water is added to the reaction mass.

The reaction mass is then extracted with three 200 ml portions of toluene. The aqueous layer is acidified and re-extracted with two 100 ml portions of toluene. The toluene extracts are combined and washed with three 50 ml portions of 20% aqueous NaCl followed by one 40 ml portion of 10% sodium acetate. The reaction product so treated is then evaporated to remove the toluene solvent. It is then fractionally distilled using a semi-micro still a 72°–74° C and 5 mm Hg. pressure.

| NMR Analysis | Interpretation | |
|---|---|---|
| 12.00 ppm (s) | $-\underset{\underset{O}{\parallel}}{C}-O-H$ | 1H |
| 6.00–5.60 (m) | $HC=CH_2$ | 1H |
| 5.18–5.02 (m) | $HC=CH_2$ | 2H |
| 2.76–2.04 (m) | $\{=C-CH_2- + Me-CH-C=O\}$ | 3H |
| 1.19 (d) | $CH_3-CH-C=O$ | 3H |

IR Analysis
915 cm$^{-1}$
990
1210
1240
1280
1415
1430
1640
1700
2660
2940
2980
3080

EXAMPLE III

Preparation of Ethyl-2-Methyl-3,4-Pentadienoate

Reaction:

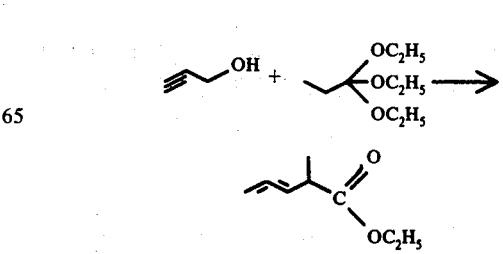

Into a 2 liter autoclave, the following materials are placed:

| Ingredient | Parts by Weight |
|---|---|
| Triethyl orthopropionate | 495 grams |
| 2-Propyn-1-ol | 90 grams |
| Propionic acid | 12 grams |

The autoclave is closed and the reaction mass is heated to 150° C (over a period of 50 minutes). The reaction mass is then maintained at a temperature of between 135°–160° C and at a pressure of 20 up to 60 psig for a period of 3 hours. At the end of this 3-hour period, the autoclave is opened and the reaction mass is cooled to room temperature. 12.6 g of sodium bicarbonate is then added to the reaction mass in order to neutralize the propionic acid. 30 g of Primol[R] (see Note 1) and 0.1 g of Ionol[R] (see Note 2) are added and the resulting reaction product is fractionally distilled at atmospheric pressure to a pot temperature of 129° C. A mixture of ethanol and ethyl propionate is distilled over. Vacuum is then applied to the distillation column and the resultant product, ethyl-2-methyl-3,4-pentadienoate is distilled at a vapor temperature of 65°–69° C at a pressure of 24–33 mm Hg as fractions 5-10 of the following fractions:

| Fraction No. | Vapor Temperature | Liquid Temperature | Pressure (mm Hg) | Weight of Fraction | Reflux Ratio |
|---|---|---|---|---|---|
| 1 | 68–72° C | 127–87° C | 760 | 174.5 g | 9:1 |
| 2 | 28–42 | 86–83 | 48–50 | 19.4 | 9:1 |
| 3 | 69 | 84 | 45 | 12.6 | 9:1 |
| 4 | 65 | 79 | 34 | 20.1 | 9:1 |
| 5 | 67 | 80 | 33 | 38.9 | 4:1 |
| 6 | 67 | 82 | 33 | 32.5 | 4:1 |
| 7 | 67 | 82 | 33 | 36.8 | 4:1 |
| 8 | 67 | 83 | 33 | 37.2 | 4:1 |
| 9 | 66 | 84 | 24 | 39.8 | 4:1 |
| 10 | 65 | 94 | 24 | 36.9 | 4:1 |
| 11 | 57 | 108 | 10 | 45.5 | 4:1 |
| 12 | 39 | 172 | 2.3 | 14.5 | 4:1 |

Note 1: Primol[R] is a registered trademark identifying a hydrocarbon mineral oil produced by Exxon Corp. of Linden, New Jersey.
Note 2: Ionol[R] is a registered trademark identifying the compound 2,6-di-t-butyl-4-methyl phenol.

The resulting material is confirmed by IR, NMR and mass spectral analyses to have the structure:

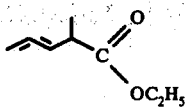

Mass spectral analysis:
Parent Peak, then in order of decreasing intensity:
m/e = 140(M+); 67, 97, 29, 41, 125

| Nuclear Magnetic Resonance Analysis: | | |
|---|---|---|
| ppm | Interpretation | |
| 1.26 (t) | $CH_3-C-O-C-$ with $\|\|$ O | 6H |
| 1.28 (d) | $CH_3-C-C-$ with $\|\|$ O | 6H |
| 3.10 (m) | $=C-CH-C=O$ | 1H |
| 4.12 (q) | $CH_3-CH_2-O-C-$ with $\|\|$ O | 2H |
| 4.76 (m) | $H_2C=C=C-$ | 2H |
| 5.40 (m) | $C=C=CH$ | 1H |

Infra Red Analysis:
Peaks
850 cm$^{-1}$
1050
1175
1225
1375
1425
1730
1950
2880
2925
2975

EXAMPLE IV

Hydrogenation of Ethyl-2-Methyl-3,4-Pentadienoate Using Thereby Lindlar Catalyst, thereby Preparing Mixtures of Ethyl-2-Methyl-Cis-3-Pentenoate and Ethyl-2-Methyl-4-Pentenoate Reaction:

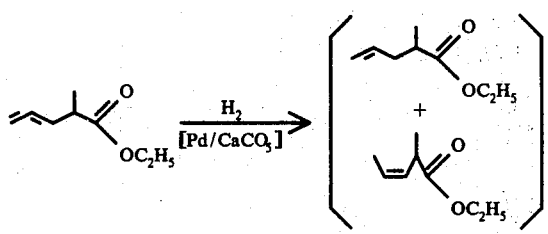

Into a 2-liter autoclave, the following ingredients are placed:

| Ingredient | Quantity |
| --- | --- |
| Ethyl-2-methyl-3,4-pentadienoate produced according to the process of Example III | 577.8 grams |
| 5 % Palladium on calcium carbonate catalyst (Lindlar catalyst) | 1.4 grams |

The autoclave is connected by means of pressure tubing to a hydrogen containing cylindar. The autoclave is then sealed and while adding hydrogen into the autoclave from the hydrogen containing cylindar and maintaining the pressure within the autoclave at 60 pounds per square inch gauge the reaction mass is stirred. During the hydrogenation and over a 19-hour period, the reaction mass is maintained at room temperature by means of the application of cooling. At the end of the 19-hour period, the autoclave is opened; and an additional 1.4 grams of Lindlar catalyst is added. The autoclave is then closed and hydrogen is continuously added thereto while stirring the reaction mass over an additional reaction period of 10 hours. At the end of the 10-hour period, the autoclave is opened, and the reaction mass is filtered. An additional 2.8 grams Lindlar catalyst is then added to the reaction mass which is then again placed in the autoclave with hydrogen being added thereto and pressure being maintained at 60 pounds per square inch gauge. At the end of one and three-quarter hours, GLC analysis indicates that the reaction is completed. The autoclave is then opened and the reaction mass is filtered. The filtered reaction mass is then distilled on a 1 inch × 1 foot Goodloe distillation column after adding thereto 10 grams of Primol$^R$ (see note 1) and 0.1 grams of Ionol$^R$ (see note 2) yielding the following fractions.

Note 1: Primol$^R$ is a registered trademark identifying a hydrocarbon mineral oil produced by Exxon Incorporation of Linden, New Jersey.
Note 2: Ionol$^R$ is a registered trademark identifying the compound 2,6-di-tert-butyl-4-methylphenol.

| Fraction No. | Vapor Temp. | Liquid Temp. | Vacuum (mm Hg Pressure) | Weight of Fraction | Reflux Ratio |
| --- | --- | --- | --- | --- | --- |
| 1 | 31–33° C | 77–86° C | 200.0–205.0 | 8.2 g | 19:1 |
| 2 | 60 | 90 | 200.0 | 17.0 | 19:1 |
| 3 | 61 | 93 | 200.0 | 11.0 | 19:1 |
| 4 | 62 | 97 | 200.0 | 12.6 | 19:1 |
| 5 | 62 | 100 | 200.0 | 13.6 | 19:1 |
| 6 | 62 | 107 | 200.0 | 13.5 | 19:1 |
| 7 | 62 | 111 | 200.0 | 14.3 | 19:1 |
| 8 | 65 | 115 | 200.0 | 12.5 | 19:1 |
| 9 | 81 | 119 | 200.0 | 13.1 | 19:1 |
| 10 | 88–110 | 116–117 | 205 | 6.6 | 19:1 |
| 11 | 112 | 117 | 205 | 6.0 | 19:1 |
| 12 | 113 | 117 | 205 | 6.2 | 19:1 |
| 13 | 113 | 118 | 205 | 7.0 | 19:1 |
| 14 | 114 | 118 | 205 | 4.5 | 19:1 |
| 15 | 114 | 118 | 205 | 17.8 | 9:1 |
| 16 | 114 | 118 | 205 | 21.5 | 9:1 |
| 17 | 114 | 118 | 205 | 23.9 | 9:1 |
| 18 | 114 | 118 | 205 | 21.2 | 9:1 |
| 19 | 115 | 120 | 205 | 24.5 | 9:1 |
| 20 | 115 | 120 | 205 | 23.2 | 9:1 |
| 21 | 115 | 120 | 205 | 10.0 | 9:1 |
| 22 | 114–115 | 119–120 | 200–205 | 20.8 | 9:1 |
| 23 | 115 | 121 | 205 | 20.8 | 9:1 |
| 24 | 115 | 121 | 205 | 15.0 | 9:1 |
| 25 | 115 | 122 | 205 | 19.3 | 9:1 |
| 26 | 115 | 124 | 205 | 17.9 | 9:1 |
| 27 | 116 | 125 | 205 | 21.9 | 9:1 |
| 28 | 116 | 128 | 205 | 18.9 | 9:1 |
| 29 | 116 | 131 | 205 | 19.0 | 4:1 |
| 30 | 116 | 144 | 205 | 24.6 | 4:1 |
| 31 | 116 | 160 | 205 | 13.5 | 4:1 |
| 32 | 111 | 200 | 205 | 6.1 | 4:1 |

Fractions 12, 13, 14, 21, 23 and 31 are analyzed using GLC analysis (conditions: 10 feet × ¼ inch Carbowax 20M column programmed at 120°–150° C).

| Fraction No. | Weight of Fraction | Percentage of ethyl-2-methyl-cis-3-pentenoate | Percentage of ethyl-2-methyl-4-pentenoate |
| --- | --- | --- | --- |
| 12 | 6.2 g | 57.6 % | 41.6 % |
| 13 | 7.0 g | 59.2 % | 38.9 % |
| 21 | 10.0 g | 70.9 % | 28.7 % |
| 23 | 20.8 g | 75.6 % | 24.1 % |
| 31 | 13.5 g | 93.8 % | 4.9 % |

Analyses
a. Ethyl-2-methyl-cis-3-pentenoate
  i. Mass Spectral Analysis: Parent Peak; then in decreasing order of intensity: m/e = 142(M$^+$); 69, 41, 29, 27, 39, 68.
  ii. NMR Analysis:

| ppm | Interpretation |
| --- | --- |
| 1.18 (d) | =C—C(CH$_3$)—C=O |
| 1.22 (t) | CH$_3$—C—O |
| 1.64 (d) | =C—CH$_3$ |
| 3.40 (m) | =C—C(H)—C=O |
| 4.10 (q) | —CH$_2$—O—C(=O)— |
| 5.20 (m) | HC=CH |

Infrared Analysis:
710, 860, 960, 1020, 1045, 1090, 1140, 1175, 1240, 1325, 1370, 1395, 1450, 1650, 1730, 2880, 2900, 2940, 2980, 3020 cm$^{-1}$ b. ethyl-2-methyl-4-pentenoate Mass Spectral Analysis: Parent Peak then in decreasing order of intensity: m/e = 142(m$^+$); 69, 41, 29, 27, 39, 68.

NMR Analysis:

| ppm | Interpretation | |
| --- | --- | --- |
| 1.16 ppm (d) | CH$_3$—C(H)—C(=O)— | 6H |
| 1.20 (t) | CH$_3$—CH$_2$—O—C(=O)— | |
| 2.64–2.08 (m) | =C—CH$_2$ + HC(=O)— | 3H |
| 4.12 (q) | Me—CH$_2$—O—C(=O)— | 2H |
| 5.18–4.98 (m) | HC=CH$_2$ | 2H |
| 5.98–5.56 (m) | HC=CH$_2$ | 1H |

Infrared Analysis:
710, 860, 960, 1020, 1045, 1090, 1140, 1175, 1240, 1325, 1370, 1395, 1450, 1650, 1730, 2880, 2900, 2940, 2980, 3020 cm$^{-1}$

EXAMPLE V

Hydrgenation of Ethyl-2-Methyl-3,4-Pentadienoate Using a 5% Palladium on Carbon Catalyst Reaction:

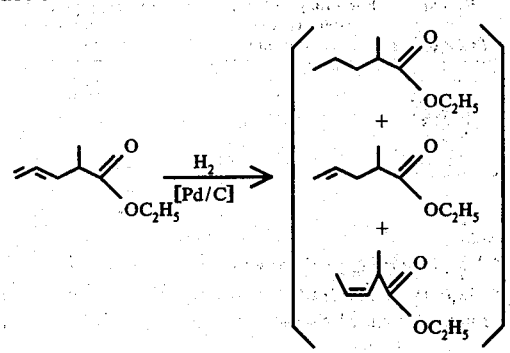

Into a 250 cc Parr Bomb the following ingredients are placed:

| Ingredient | Amount | |
|---|---|---|
| Ethyl-2-methyl-3,4-pentadienoate produced according to the process of Example III | 25 | grams |
| 5 % Palladium on Carbon | 0.025 | grams |

The Parr Bomb is connected by means of pressure tubing to a hydrogen-containing cylinder. The Parr Bomb is then sealed while adding hydrogen thereinto from the hydrogen-containing cylinder and maintaining pressure within the Parr Bomb at 25–50 psig. The reaction is maintained at room temperature using external cooling. After a period of 3.5 hours, the Parr Bomb is opened and the contents are filtered. GLC analysis indicates that the reaction is complete. GLC Analysis (Conditions: 8 feet × ½ inch carbowax column; column temperature 120° C) indicates presence of the following components in the following weight percentages:

| Component | Weight Percent |
|---|---|
| Ethyl-2-methyl-cis-3-pentenoate | 65.7 % |
| Ethyl-2-methyl-4-pentenoate | 14.3 % |
| Ethyl-2-methyl pentanoate | 19.9 % |

EXAMPLE VI

Tobacco Formulation

A tobacco mixture is produced by admixing the following materials:

| Ingredient | Parts by Weight |
|---|---|
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.
The following flavor formulation is prepared:

| Ingredient | Parts by Weight |
|---|---|
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above-stated tobacco flavor formulation is applied at the rate of 0.1% to all of the cigarettes produced using the above tobacco formulation. Half of the cigarettes are then treated with 100 and 200 ppm of 2-methyl-4-pentenoic acid produced according to the process of Example II. The control cigarettes not containing the 2-methyl-4-pentenoic acid produced according to the process of Example II and the experimental cigarettes which contain the 2-methyl-4-pentenoic acid produced according to the process of Example II are evaluated by paired comparison and the results are as follows:

The experimental cigarettes are found to be, on smoking, more aromatic in aroma.

In the smoke, the experimental cigarettes are found to be more aromatic, sweeter, more bitter, less harsh in the mouth and throat and leave a slight sweet chemical mouth coating effect similar to Turkish tobacco. All cigarettes are evaluated for smoke flavor with a 20 mm cellulose acetate filter.

The 2-methyl-4-pentenoic acid produced according to the process of Example II enhances the tobacco-like taste and aroma of the blended cigarette and gives the cigarette a Turkish-like character.

EXAMPLE VII

Tobacco Flavor Formulation and Tobacco

A tobacco mixture is produced by admixing the following materials:

| Ingredient | Parts by Weight |
|---|---|
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.
The following flavor formulation is prepared:

| Ingredient | Parts by Weight |
|---|---|
| Ethyl butyrate | .05 |
| Ethyl valerate | .05 |
| Maltol | 2.00 |
| Cocoa extract | 26.00 |
| Coffee extract | 10.00 |
| Ethyl alcohol (95 % aqueous) | 20.00 |
| Water | 41.90 |

The above-stated tobacco flavor formulation is applied at the rate of 0.1% to all of the cigarettes produced using the above tobacco formulation. Half of the cigarettes are then treated with 100 or 200 ppm of the mixture containing ethyl-2-methyl-4-pentenoate produced according to the process of Example I.

The control cigarettes not containing the ethyl-2-methyl-4-pentenoate produced according to the process of Example I and the experimental cigarettes which do contain the ethyl-2-methyl-4-pentenoate produced according to the process of Example I are evaluated by paired comparison, and the results are as follows:

In aroma, the cigarettes containing the mixture having ethyl-2-methyl-4-pentenoate have been found to be more aromatic.

In smoke flavor, the cigarettes containing the mixture having ethyl-2-methyl-4-pentenoate are more aromatic, more sweet, more bitter, slightly less harsh in the mouth and throat and leave a slight, sweet chemical mouth-coating effect similar to Turkish tobacco.

In summary, the mixture having ethyl-2-methyl-4-pentenoate enhances the tobacco-like taste and aroma of a blended cigarette and imparts to that cigarette a Turkish-like character is smoke flavor.

EXAMPLE VIII

Tobacco Flavor Formulation and Tobacco

A tobacco mixture is produced by admixing the following materials:

| Ingredient | Parts by Weight |
| --- | --- |
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.
The following flavor formulation is prepared:

| Ingredient | Parts by Weight |
| --- | --- |
| Ethyl butyrate | .05 |
| Ethyl valerate | .05 |
| Maltol | 2.00 |
| Cocoa extract | 26.00 |
| Coffee extract | 10.00 |
| Ethyl alcohol (95 % aqueous) | 20.00 |
| Water | 41.90 |

The above-stated tobacco flavor formulation is applied at the rate of 0.1% to all of the cigarettes produced using the above tobacco formulation. Half of the cigarettes are then treated with 100 or 200 ppm of the mixture containing ethyl-2-methyl-4-pentenoate produced according to the process of Example IV. (Bulked fractions 12 and 13).

The control cigarettes not containing the ethyl-2-methyl-4-pentenoate mixture produced according to the process of Example IV and the experimental cigarettes which do contain the ethyl-2-methyl-4-pentenoate mixture produced according to the process of Example IV are evaluated by paired comparison, and the results are as follows:

In aroma, the cigarettes containing the mixture having ethyl-2-methyl-4-pentenoate have been found to be more aromatic.

In smoke flavor, the cigarettes containing the mixture having the ethyl-2-methyl-4-pentenoate mixture are more aromatic, more sweet, more bitter, slightly less harsh in the mouth and throat and leave a slight, sweet chemical mouth-coating effect similar to Turkish tobacco.

In summary, the mixture having ethyl-2-methyl-4-pentenoate enhances the tobacco-like taste and aroma of a blended cigarette and imparts to that cigarette a Turkish-like character in smoke flavor.

EXAMPLE IX

Tobacco Flavor Formulation and Tobacco

A tobacco mixture is produced by admixing the following materials:

| Ingredient | Parts by Weight |
| --- | --- |
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.
The following flavor formulation is prepared:

| Ingredient | Parts by Weight |
| --- | --- |
| Ethyl butyrate | .05 |
| Ethyl valerate | .05 |
| Maltol | 2.00 |
| Cocoa extract | 26.00 |
| Coffee extract | 10.00 |
| Ethyl alcohol (95 % aqueous) | 20.00 |
| Water | 41.90 |

The above-stated tobacco flavor formulation is applied at the rate of 0.1% to all of the cigarettes produced using the above tobacco formulation. Half of the cigarettes are then treated with 100 or 200 ppm of the mixture containing ethyl-2-methyl-4-pentenoate produced according to the process of Example V.

The control cigarettes not containing the mixture containing ethyl-2-methyl-4-pentenoate produced according to the process of Example V and the experimental cigarettes which do contain the mixture containing ethyl-2-methyl-4-pentenoate produced according to the process of Example V are evaluated by paired comparison, and the results are as follows:

In aroma, the cigarettes containing the mixture containing ethyl-2-methyl-4-pentenoate have been found to be more aromatic.

In smoke flavor, the cigarettes containing the mixture having ethyl-2-methyl-4-pentenoate are more aromatic, more sweet, more bitter, slightly less harsh in the mouth and throat and leave a slight, sweet chemical mouth-coating effect similar to Turkish tobacco.

In summary, the mixture having ethyl-2-methyl-4-pentenoate enhances the tobacco-like taste and aroma of a blended cigarette and imparts to that cigarette a Turkish-like character in smoke flavor.

What is claimed is:

1. A process for augmenting or enhancing the organoleptic properties of smoking tobacco comprising the step of adding to smoking tobacco homogenized tobacco containing from 50 up to 250 ppm of a flavoring composition comprising a compound having the structure:

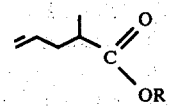

wherein R is hydrogen or ethyl, and at least one tobacco flavoring additive selected from the group consisting of:
  Esters;
  Pyrones;
  Aldehydes;
  Ketones;
  Acetals;
  Natural oils and extracts;
  Lactones;
  Ethers;
  Pyrazines; and
  Pyrroles.

2. A smoking tobacco article comprising smoking tobacco and from 50 up to 250 ppm of a compound having the structure:

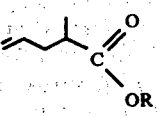

wherein R is hydrogen or ethyl.

* * * * *

UNITED STATES PATENT AND TRADEMARK OFFICE
CERTIFICATE OF CORRECTION

PATENT NO. : 3,987,803
DATED : October 26, 1976
INVENTOR(S) : JOHN B. HALL, CHING Y. TSENG, MANFRED HUGO VOCK, JOAQUIN VINALS, AND EDWARD J. SHUSTER It is certified that error appears in the above-identified patent and that said Letters Patent are hereby corrected as shown below:

Col. 3, line 20, the "propanol-1" should read "propenol-1".

Col. 3, line 25, the word "2-propanol-1" should read "2-propenol-1".

Col. 4, line 4, the word "2-propane-1" should read -- 2-propynol-1 --.

Signed and Sealed this

Seventeenth Day of May 1977

[SEAL]

Attest:

RUTH C. MASON
Attesting Officer

C. MARSHALL DANN
Commissioner of Patents and Trademarks